United States Patent [19]

Polando

[11] Patent Number: 5,368,547
[45] Date of Patent: Nov. 29, 1994

[54] MEDICAL ANTI-SHOCK APPLIANCE

[76] Inventor: Gordon Polando, 3419 Maryland Rd., Apt. 212, Woodmere, Ohio 44122

[21] Appl. No.: 935,555

[22] Filed: Aug. 26, 1992

[51] Int. Cl.[5] .................................................. A61H 9/00
[52] U.S. Cl. ............................ 601/151; 128/DIG. 20; 602/13
[58] Field of Search ............... 128/24 R, 24.1, 64, 128/DIG. 20; 602/12, 13, 23; 601/15, 148–152

[56] References Cited

U.S. PATENT DOCUMENTS

| | | | |
|---|---|---|---|
| 3,288,132 | 11/1966 | Meredith | 128/64 |
| 3,867,930 | 2/1975 | Brown | 128/DIG. 15 |
| 4,091,804 | 5/1978 | Hasty | 128/24 R |
| 4,270,527 | 6/1981 | Peters et al. | 602/13 |
| 4,624,244 | 11/1986 | Taheri | 128/24 R |
| 4,624,248 | 11/1986 | Poole et al. | 602/13 |
| 4,674,479 | 6/1987 | Jennings et al. | 128/DIG. 20 |
| 4,753,226 | 6/1988 | Zheng et al. | 128/64 |
| 4,986,260 | 1/1991 | Iams et al. | 128/29 R |
| 5,117,812 | 6/1992 | McWhorter | 128/24 R |

*Primary Examiner*—Richard J. Apley
*Assistant Examiner*—Jeanne M. Mollo
*Attorney, Agent, or Firm*—John F. McDevitt

[57] ABSTRACT

A medical appliance is disclosed employing multiple inflatable components which cooperate to apply compressive pressure to each leg of a person. The appliance includes physically separate upper and lower leg components each having individual chambers joined together with flexible straps for attachment to the wearer. The appliance can further include a physically separate inflatable bladder elements for attachment to the wearer's pelvic region.

10 Claims, 1 Drawing Sheet

MEDICAL ANTI-SHOCK APPLIANCE

BACKGROUND OF THE INVENTION

This invention generally relates to an inflatable medical appliance of the type commonly employed under emergency conditions by rescue personnel to counteract the effects of internal bleeding, shock and stabilize pelvic fractures when attached to lower body portions of the person and more particularly to an improved form of said appliance having physically separate inflatable components which apply an encircling pressure to the applied body portion.

Medical anti-shock trousers (MAST) are now used in emergency situations either inside or outside of hospitals to counteract internal bleeding situations as well as stabilize certain bone fractures. In doing so, the conventional medical appliance is secured to lower body portions of an injured or sick person in order to apply a compressive pressure inhibiting further bleeding and/or shock while further immobilizing any pelvic injuries found. A known medical appliance of this type is described in U.S. Pat. No. 4,039,039 having inflatable trousers which enclose both legs of the person and further extend to encompass the abdominal region. The device has front and rear sections joined along the inseam portions of the leg segments and fitted to the wearer with releasable straps. The physically separate leg and abdominal chamber means in said device are inflated from a common gas supply source such as a foot pump or pressurized container. In U.S. Pat. No. 4,624,248 a similar garment construction for said medical appliance is formed with transparent materials enabling the covered areas of a wearer to be visually observed after the garment has been attached and inflated. The described garment also features a modular construction having the modular sections interconnected together with readily separable means such as conventional zippers to allow damaged sections to be replaced without replacing the entire garment. A further benefit said to be derived with such modular construction is ability to open the garment while inflated in order to gain access to local injuries requiring further medical attention without removing the pressure being applied elsewhere to a wearer.

To attach either of the above type garment devices to an injured or sick person requires such person to be supine with legs fully extended, thereby precluding their use in many accident situations or when the person is otherwise spatially confined, Valuable time will also be lost in moving the injured or sick person to a reclining position for attachment of the present garment devices. After inflation, covered regions of the person are also not immediately accessible without total or partial deflation of the garment. Another drawback found with such garment devices can be excessive manipulation of the person when being applied which can be most serious if a spine hip, knee or neck injury is suspected. A separate garment size can also be required for adults and children. Likewise, having the entire leg sections of such garments constructed as a single unit can require expensive repair or replacement costs.

In more recently issued U.S. Pat. No. 4,938,208 there is described a pressurized multi-chambered medical appliance which can also apply compressive pressures against the leg of a person and with said device reported to be useful when applied in pairs wrapped about both legs of the person. Each device employs a plurality of inflatable chambers enclosed in a sleeve construction extending from the upper leg of a wearer to include the wearer's foot and with the individual chambers being positioned along the sides and back of a person's leg. Understandably, such type device is again subject to many of the same shortcomings noted in connection with the garment type MAST devices now in common use so that there still remains serious need to improve the construction of an appliance serving the same general purpose.

It is therefore an object of the present invention to provide an improved medical anti-shock appliance which is more convenient and versatile to apply.

It is another object of the present invention to provide an improved medical anti-shock appliance affording greater accessibility to the wearer's injured regions after being applied, It is still another object of the present invention to provide an improved medical anti-shock appliance not limited by the physical size of a wearer.

Still another object of the present invention is to reduce the time period needed for attachment of such improved medical anti-shock appliance to an injured or sick person.

These and other objects as well as advantages of the present invention will become more apparent from the following detailed description being provided upon the preferred embodiments.

SUMMARY OF THE INVENTION

A fully effective medical anti-shock appliance has now been discovered having a far simpler construction than a conventional MAST type garment. Basically, the improved construction comprises a pair of physically separate multiple inflatable leg components for attachment to both legs of a person, each of said leg components having physically separate upper and lower leg inflatable chamber means joined together by strap means with each inflatable chamber means extending when attached only partially about the length and circumference of the applied leg portion, said inflatable chamber means also being inflated together with connecting conduit means from a common gas supply source. Attachment of such cooperating multi-part construction to the upper and lower leg portions of a wearer can be provided with conventional releasable strap means optionally adjustable in length to the physical size of the particular wearer. Such attachment can be easily and quickly carried out by medical personnel upon the injured person whether reclining or sitting in various positions which is a distinct advantage in car accidents as well as many hospital situations. The present appliance can still further include a third physically separate inflatable chamber means of conventional construction for attachment to the pelvic region of the person with said chamber also being inflated from the same gas supply source. Inflation of the chamber means after attachment of the present appliance can also proceed in the conventional manner with customary pneumatic foot pump means being employed as well as a pressurized air container. Unlike the conventional MAST type garment, the present appliance can also be employed with conventional long bone stabilization medical devices.

In preferred embodiments, the upper and lower leg inflatable chamber means employ flexible bladder elements enclosed within a fabric sheath or cover of conventional construction. The physical size of the lower leg chamber means can be kept smaller than the physical size of the upper leg chamber means to conform with the ordinary shape of a human anatomy. Having both leg chamber means smaller in physical size than the physical size of a wearer's limb further permits either or both chamber means to be attached in various spatial orientations. It becomes thereby possible to attach both smaller size leg chamber means other than to expose the front portions of a wearer's leg as well as to orient said chamber elements in skewed relationship with respect to each other. A still further multi-part construction is also preferred for both upper and lower leg chamber means in the present appliance. In doing so, a pair of bladder elements joined together horizontally with strap means for positioning on each side of the applied leg portion is employed to form each of said leg chamber means. A four-part assembly for each leg is then provided by joining together individual upper and lower leg bladder elements on the same side with vertical straps.

DETAILED DESCRIPTION OF THE PREFERRED EMBODIMENTS

Figure 1:
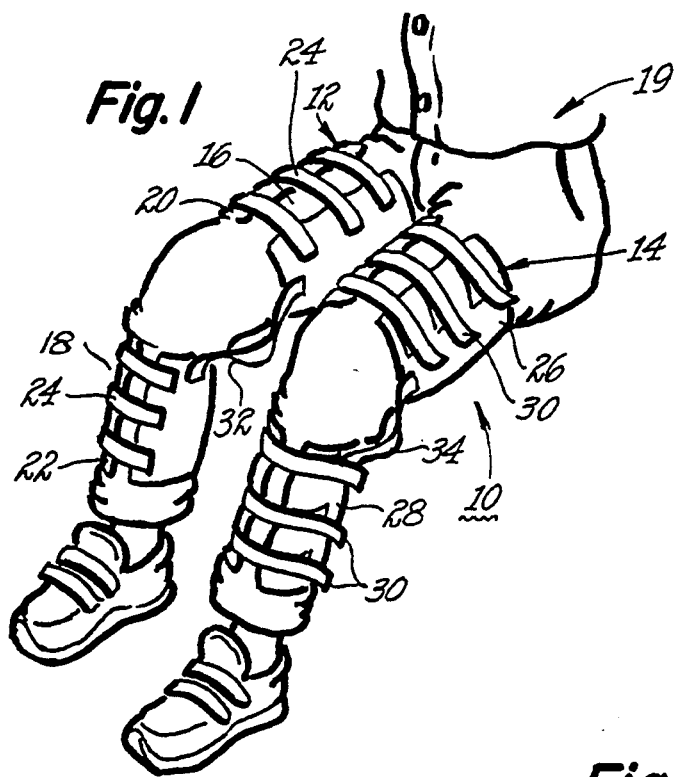
FIG. 1 is a perspective view depicting a representative medical appliance of the present invention when applied to a person.

Referring to the drawings, there is depicted in FIG. 1 a perspective view for a representative medical appliance of the present invention after having been physically attached to a sitting person. Specifically, said medical anti-shock appliance 10, comprises a pair of physically separate multi-part leg components 12 and 14 which have been each fitted around the upper and lower legs 16 and 18, respectively, of the wearer 19 without requiring any physical movement by this person to do so. Right leg component 12 comprises upper and lower leg inflatable chamber means 20 and 22, respectively, which have been wrapped about the limb of the wearer so as to extend only partially about the length and circumference of the applied leg portion. Chamber means 20 and 22 are both physically secured to the wearer's limb with multiple releasable strap means 24 constructed in a conventional manner with Velcro material or webbing and the like as well as made adjustable in length to accommodate leg size. Correspondingly, left leg component 14 includes upper and lower leg inflatable chamber means 26 and 28, respectively, each having releasable strap means 30 for physical attachment of said chamber means to the remaining limb 18. Only a partial view of the assembled chamber means can be seen in the present drawing by reason of having employed the previously mentioned multiple bladder element construction. A detailed description for said entire chamber means is provided in FIG. 2, however, including the flexible strap means being utilized to interconnect individual bladder elements in each leg component. In accordance therewith, chamber means 20 and 22 are joined to each other with straps 32 while chamber means 26 and 28 are similarly joined together with straps 34. When inflated after attachment in a manner also further described in connection with FIG. 2, the depicted medical appliance has been found, surprisingly, to function as well as the MAST garments now being used to counteract internal bleeding and shock. A comparison was made of mean arterial pressure (MAP) and heart rate (HR) readings for normovolemic persons wearing the conventional MAST garment as compared with like readings made upon the same individuals when wearing the above described device. The range from minimum resting to maximum inflation under the test conditions found the MAST garment producing HR measurements in the range 51–84 with MAP measurements residing in the range 69–113. Wearers of the above described improvement measured HR values in the range 58–84 with MAP readings in the range from 67–110.

Figure 2:
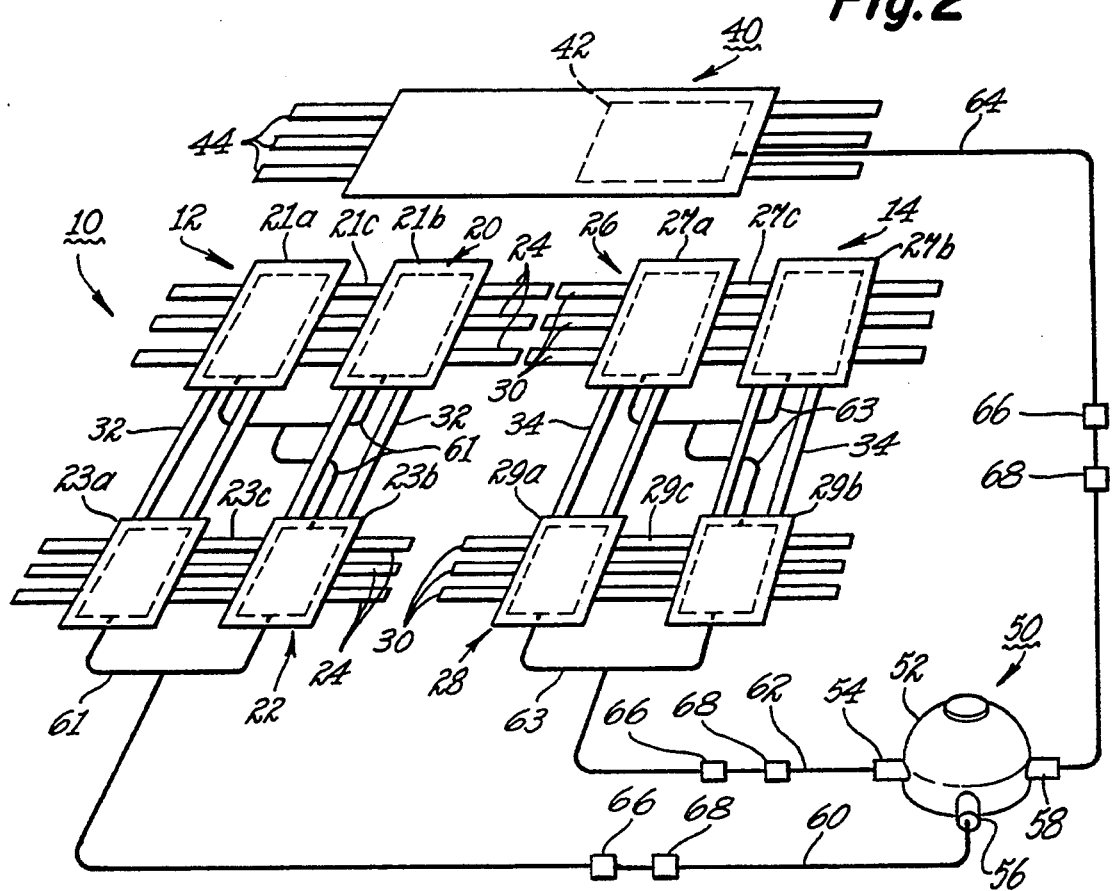
FIG. 2 is a perspective view of the FIG. 1 medical appliance depicted with typical equipment means for its inflation.

In FIG. 2, a perspective view is shown of the FIG. 1 medical appliance 10 prior to being physically attached to both wearer's legs and thereafter inflated. Further included in the present drawing for optional employment together with the present device in medical emergencies requiring stabilization of a suspected pelvic injury is an otherwise conventional physically separate inflatable chamber means 40 also shown before attachment to the injured person. Representative equipment means 50 to inflate all of the depicted chamber means together after attachment to the injured person from a common gas supply source are further included in the present drawing. Common numerals have also been retained in the present drawing for the multi-element FIG. 1 appliance as a means to more fully explain the specific details of said device construction.

Accordingly, medical appliance 10 comprises physically separate multiple bladder leg components 12 and 14 having upper and lower leg inflatable chamber means 20–22 and 26–28, respectively, for attachment to leg portions of the wearer. Upper leg chamber means 20 and 26 are shown to be larger in physical size than lower leg chamber means 22 and 28 to accommodate the shape of an ordinary human anatomy. Each of the depicted leg components 12 and 14 comprises an assembly of inflatable chamber elements physically connected together with flexible straps while further being operationally interconnected with conduit means to a common gas supply source. Upper leg chamber means 20 employs chamber elements 21a and 21b which are physically joined together with horizontal flexible straps 21c for placement along both sides of the wearer's upper right leg. Lower leg chamber means 22 includes chamber elements 23a and 23b again physically joined together with horizontal flexible straps 23c for placement along both sides of the wearer's lower right leg. As can also be seen in the present drawing, both individual chamber elements of upper chamber means 20 are further joined physically with vertical flexible straps 32 to the individual chamber elements on the same side in lower chamber means 22. Correspondingly, upper leg chamber means 26 for the wearer's left leg employs individual chamber elements 27a and 27b physically joined together horizontally with flexible straps 27c whereas lower chamber means 28 has individual chamber elements 29a and 29b joined together with horizontal flexible straps 29c. Vertical flexible straps 34 further connect individual chamber elements in said left leg assembly. Releasable straps 24 further included in the leg component 12 along with similar straps means 30 being provided in leg component 14 enables physical attachment of the described appliance to a wearer. Conventional inflatable chamber means 40 in the present embodiment also employs a single flexible bladder element 42 along with a plurality of releasable straps 44 for its attachment to the person's abdomen as a physically separate structural unit. All inflatable chamber elements in the illustrated appliance can have a similar construction wherein the flexible bladder means are enclosed within a fabric sheath in the customary manner.

Inflation of all chamber means 20, 22, 26, 28 and 40 in the present embodiment is provided with conventional foot pump means 50. A foot operated pump 52 includes multiple outlets 54, 56 and 58 for separate connection to the chamber means of both leg components as well as to the abdomen chamber means 40. A first flexible conduit 60 extends from said common gas supply source to inflate both upper and lower leg inflatable chamber means of leg component 12 whereas a second flexible conduit 62 is interconnected in the same manner to remaining leg component 14. As can be noted regarding interconnection of said conduit means with respect to upper and lower leg chamber means of an individual leg component, there exists a serial connection from the common gas supply source which proceeds first to the chamber elements of the lower leg component and then proceeds to the chamber elements of the upper leg component. Inflation of said chamber means in such manner was provided in the present embodiment with conventional rubber tubing 61 and 63. Third flexible conduit means 64 provides direct and concurrent inflation of bladder elements 42 in the remaining inflatable pelvic component 40. Understandably, various other known inflatable chamber constructions together with different means to inflate such constructions from a common gas supply source can also be employed with comparable results in the presently improved appliance. Conventional pressure relief valves 66 and manual shut-off valves 68 have also been provided optionally in each of the illustrated conduit means.

It will be apparent from the foregoing description that a broadly useful and novel means has been provided to apply encircling pressure to lower body portions of a person either inside or outside of a hospital. It is contemplated that modifications can be made in the present medical appliance herein illustrated, however, without departing from the true spirit and scope of the present invention. For example, buckles and other type fastening means can be incorporated in the releasable straps being employed to either physically interconnect or secure the inflatable chamber elements of the present device to the person. Likewise, one or more conventional pressure sensing gauges are contemplated for employment in the present device to measure the encircling pressure being applied. Consequently, it is intended to limit the present invention only by the scope of the following claims.

What I claim as new and desire to secure by Letters Patent of the United States is:

1. A medical anti-shock appliance of the type employed under emergency conditions by rescue personnel to counteract the effects of internal bleeding and shock when attached to lower body portions of a person comprising a pair of physically separate inflatable leg components for attachment to both legs of the person, each of said leg components having physically separate upper and lower leg inflatable chamber means joined together by first strap means and with each inflatable chamber means adapted to extend when attached only partially about the length and circumference of the applied leg portion, said inflatable chamber means each having physically separate bladder elements joined together by separate strap means with said inflatable chamber means also being simultaneously inflated together with interconnecting conduit means from a common gas supply source, and with said interconnecting conduit means comprising a first conduit means operably connected to the common gap supply source at a first end and operably connected to the lower leg inflatable chamber means on each leg of the person at a second end and a second conduit means operably connected to the lower leg inflatable chamber means at a first end and operably connected to the respective upper leg inflatable chamber means at a second end for allowing simultaneous inflation of the lower leg and upper leg inflatable chamber means.

2. The appliance of claim 1 which further includes a physically separate inflatable chamber means for attachment to the pelvic region of the person, said chamber also being inflated from the same gas supply source, and with said physically separate inflatable chamber means being operably connected to said common gas supply source with third conduit means being connected at a first end to said common gas supply source while being connected at a second end to said physically separate inflatable chamber means.

3. The appliance of claim 1 wherein the leg components are attached to the person with releasable strap means.

4. The appliance of claim 3 wherein the releasable strap means can be adjusted in length.

5. The appliance of claim 1 wherein the lower leg chamber means are smaller in physical size than the upper leg chamber means.

6. The appliance of claim 1 wherein the common gas supply source is a pressurized air tank.

7. The appliance of claim 1 wherein the common gas supply source is a pneumatic foot pump.

8. The appliance of claim 1 wherein the chamber means include flexible bladder means enclosed within a fabric sheath.

9. The appliance of claim 1 wherein the interconnecting conduit means include shut-off valve means.

10. The appliance of claim 1 wherein the interconnecting conduit means include pressure relief valve means.

* * * * *